United States Patent [19]

Yano et al.

[11] Patent Number: 5,281,683

[45] Date of Patent: Jan. 25, 1994

[54] PROCESS FOR PRODUCING WATER-ABSORBENT RESIN

[75] Inventors: Kazutaka Yano; Yoshio Irie, both of Himeji, Japan

[73] Assignee: Nippon Shokubai Co., Ltd., Osaka, Japan

[21] Appl. No.: 989,658

[22] Filed: Dec. 14, 1992

[30] Foreign Application Priority Data

Dec. 18, 1991 [JP] Japan .................. 3-335335

[51] Int. Cl.$^5$ .......................................... C08F 120/10
[52] U.S. Cl. ................................ 526/323.2; 526/320
[58] Field of Search ............... 526/323.2, 320

[56] References Cited

U.S. PATENT DOCUMENTS

| | | | |
|---|---|---|---|
| 4,302,381 | 11/1981 | Omura et al. | 526/323.2 |
| 4,351,922 | 9/1982 | Yoshida et al. | 525/116 |
| 4,452,996 | 6/1984 | Yokoshima et al. | 526/323.2 |
| 4,912,185 | 3/1990 | Toh | 526/323.2 |

FOREIGN PATENT DOCUMENTS

| | | | |
|---|---|---|---|
| 0067379 | 12/1982 | European Pat. Off. | 526/323.2 |
| 0018601 | 2/1983 | Japan | 526/320 |
| 59-136310 | 8/1984 | Japan | 526/323.2 |
| 59-136311 | 8/1984 | Japan | 526/323.2 |
| 62-59612 | 3/1987 | Japan | 526/323.2 |
| 62-59613 | 3/1987 | Japan | 526/323.2 |
| 62-187712 | 8/1987 | Japan | 526/323.2 |
| 62-56888 | 11/1987 | Japan . | |

Primary Examiner—Joseph L. Schofer
Assistant Examiner—N. Sarofim
Attorney, Agent, or Firm—Armstrong, Westerman, Hattori, McLeland & Naughton

[57] ABSTRACT

A water-absorbent resin having high absorption capacity and a slight amount of water-soluble ingredients is produced by a process, which includes polymerizing a water-soluble monoethylenic unsaturated monomer in the presence of a crosslinking agent, and using a bifunctional compound represented by the following general formula ① as the crosslinking agent;

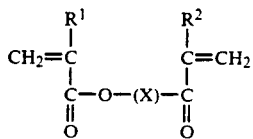

wherein $R^1$ and $R^2$ are a hydrogen atom or a methyl group independently, and —(X)— is a divalent organic group combined in a straight chain type by an optional arrangement of a structural unit (A) of —(CO—CH=CH—CO—O)$_L$— and $l=1-5$, a structural unit (B) of —(CH$_2$CH$_2$O)$_m$— and $m=2-100$, and a structural unit (C) of —(R$^3$O)$_n$— and $n=0-20$, in which $R^3$ is a $C_3$-$C_4$ alkylene.

4 Claims, No Drawings

PROCESS FOR PRODUCING WATER-ABSORBENT RESIN

BACKGROUND OF THE INVENTION

The present invention relates to a process for producing a water-absorbent resin. In detail, this invention relates to a process for producing a water absorbent resin, which has high absorption capacity and in which water-soluble ingredients are contained in only a small amount.

The water-absorbent resin has been so far used for various kinds of water-absorbent materials such as a paper diaper (or a disposable diaper), physiological articles, a soil water-retentive agent. As a water-absorbent resin of this type, there have been known a hydrolysis product of a starch-acrylonitrile graft copolymer, a neutralized product of a starch-acrylic acid graft copolymer, a crosslinked product of acrylic acid or an acrylate polymer, a partially crosslinked product of polyethylene oxide, a crosslinked product of carboxymethylcellulose and the like. Why the crosslinked polymer is used as a water-absorbent resin is to prevent conversion into a sol by its infinite swelling in absorbing water followed by swelling.

In the above-described crosslinked polymers, a crosslinked polymer obtained by copolymerizing a water-soluble monoethylenic unsaturated monomer such as acrylic acid in the presence of a crosslinking agent is of low cost as raw materials, superior in water-absorbent properties, and needs not to care about decomposition, so that it is a main current of the water-absorbent resin.

Preferable crosslinking agents so far known are N,N'-methylenebis(meth)acrylamide, N-methylol(meth)acrylamide, (poly)ethylene glycol di(meth)acrylate or (poly)propylene glycol di(meth)acrylate (refer to U.S. Pat. No. 4,351,922), glycerol tri(meth)acrylate, trimethylolpropane tri(meth)acrylate, triallylamine, triallyl cyanurate, triallyl phosphate, di(2-acryLoyloxyethyl) acid phosphate (refer to JP-B-62-56888), glycidyl (meth)acrylate, polyethylene glycol diglycidyl ether (refer to U.S. Pat. No. 4,351,922), glycerol and the like.

The real situation of conventional water-absorbent resins produced by using the aforementioned crosslinking agents is that, as the absorption capacity becomes higher, the amount of water-soluble ingredients becomes larger. If such a water-absorbent resin having a large amount of water-soluble ingredients is used for a diaper and the like during a long time, there is a problem that a slime generates on the diaper surface, and another problem that the liquid permeability becomes bad and thereby, the water-absorbent capacity and liquid-dispersing character decrease, so that a leak easily occurs. Conversely, if reduction of the water-soluble ingredients in a water-absorbent resin is intended by increase of the amount of a crosslinking agent, the water-absorbent capacity decreases and an usable range of the water-absorbent resin is limited.

SUMMARY OF THE INVENTION

According to the aforementioned real situation, an object of the present invention is to provide a process similar to conventional one, which can produce a water-absorbent resin having high absorption capacity and being slight in the amount of water-soluble ingredients.

The present inventors, as a result of intensive research carried out to attain the above object, found that a water-absorbent resin having high absorption capacity and being slight in the amount of water-soluble ingredients is obtained by copolymerizing a water-soluble ethylenic unsaturated monomer in the presence of a crosslinking agent having a specific structure which has not been employed for producing conventional water-absorbent resins, and thus, the present invention was led to completion.

Accordingly, the present invention provides a process for producing a water-absorbent resin, comprising polymerizing a water-soluble monoethylenic unsaturated monomer in the presence of a crosslinking agent, wherein said crosslinking agent is a compound represented by the following general formula ① (hereinafter, this compound is referred to as "crosslinking agent (I)").

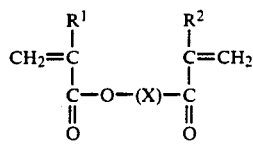

[In the formula ①, $R^1$ and $R^2$ denote a hydrogen atom or a methyl group independently; —(X)— denotes a divalent organic group combined in a straight chain type by an optional arrangement of a structural unit (A) represented by 1 to 5 units of —(CO—CH=CH—CO—O)—, a structural unit (B) represented by 2 to 100 units of —CH$_2$CH$_2$O— and a structural unit (C) represented by 0 to 20 units of —R$^3$O— (here, $R^3$ is a C$_3$-C$_4$ alkylene).]

The water-soluble monoethylenic unsaturated monomer used in this invention has no limitation as far as it has one ethylenic unsaturated group and it is soluble in water; and its preferable examples are monomers containing an acid group such as (meth)acrylic acid, itaconic acid, 2-(meth)acryloylethanesulfonic acid, 2-(meth)acryloylpropanesulfonic acid, 2-(meth)acrylamido-2-methylpropanesulfonic acid, vinylsulfonic acid, styrenesulfonic acid and the like; metal salts, ammonium salts and amine salts of the aforementioned monomers containing an acid group; monomers containing a nonionic hydrophilic group such as (meth)acrylamide, 2-hydroxyethyl (meth)acrylate, 2-hydroxypropyl (meth)acrylate, polyethylene glycol (meth)acrylate, alkoxypolyethylene glycol (meth)acrylate and the like; monomers containing an amino group such as diethylaminoethyl (meth)acrylate, diethylaminopropyl (meth)acrylate, dimethylaminopropyl (meth)acrylamide and the like; quaternary salts of the aforementioned monomers containing an amino group and the like. One kind or two or more kinds of compounds selected from the above groups of compounds can be used.

A preferable water-soluble monoethylenic unsaturated monomer is a monomer containing an acid group and an especially preferable one is at least one kind selected from acrylic acid, methacrylic acid, and their alkali metal salts, ammonium salts and amine salts. In these salts, a neutralizing percent of from 30 to 80% is preferred. This neutralization may be carried out after polymerization.

In a range of not very damaging the performance of water-absorbent resins obtained by this invention, other kinds of monomers may be jointly used, and also, the polymerization may be carried out by adding a natural polymer, such as starch, cellulose, or synthetic polymer or the like as a graft conversion component to the water-soluble monoethylenic unsaturated monomer. Preferable other kinds of monomers which can be jointly used with the water-soluble monoethylenic unsaturated monomer are, for example, methyl (meth)acrylate, ethyl (meth)acrylate, butyl (meth)acrylate, vinyl acetate, vinyl propionate and the like; and these compounds may be used alone or in combination of two or more kinds.

The crosslinking agent (I) used in this invention is a compound represented by the above-described general formula ①. In this general formula ①, a case where the number of the structural unit (A) is more than 5, a case where the number of the structural unit (B) is less than 2, a case where the number of the structural unit (B) is more than 100, and a case where the number of the structural unit (C) is more than 20; in these cases, a water-soluble ingredient for the water-absorbent capacity of an obtaining water-absorbent resin increases. A preferable total number of the structural units of (B) and (C) is in a range of from 2 to 60, and a more preferable one is in a range of from 2 to 40. The structural unit (A) may be either a cis type (a maleate structural unit) or a trans type (a fumarate structural unit).

Preferable examples of the crosslinking agent (I) are such as represented by the following chemical formulae of from (1-a) to (1-h), and these compounds are used alone or in combination of two or more kinds. However, in the crosslinking agents represented by the chemical formulae of (1-e) and (1-h), the unit shown by $-CH_2CH_2O-$ needs not to combine with the unit of $-CH_2CH(CH_3)O-$ or the unit of $-CH_2CH_2CH_2CH_2O-$ in a block type, and such as combined by an optional arrangement can be used as an equivalent crosslinking agent.

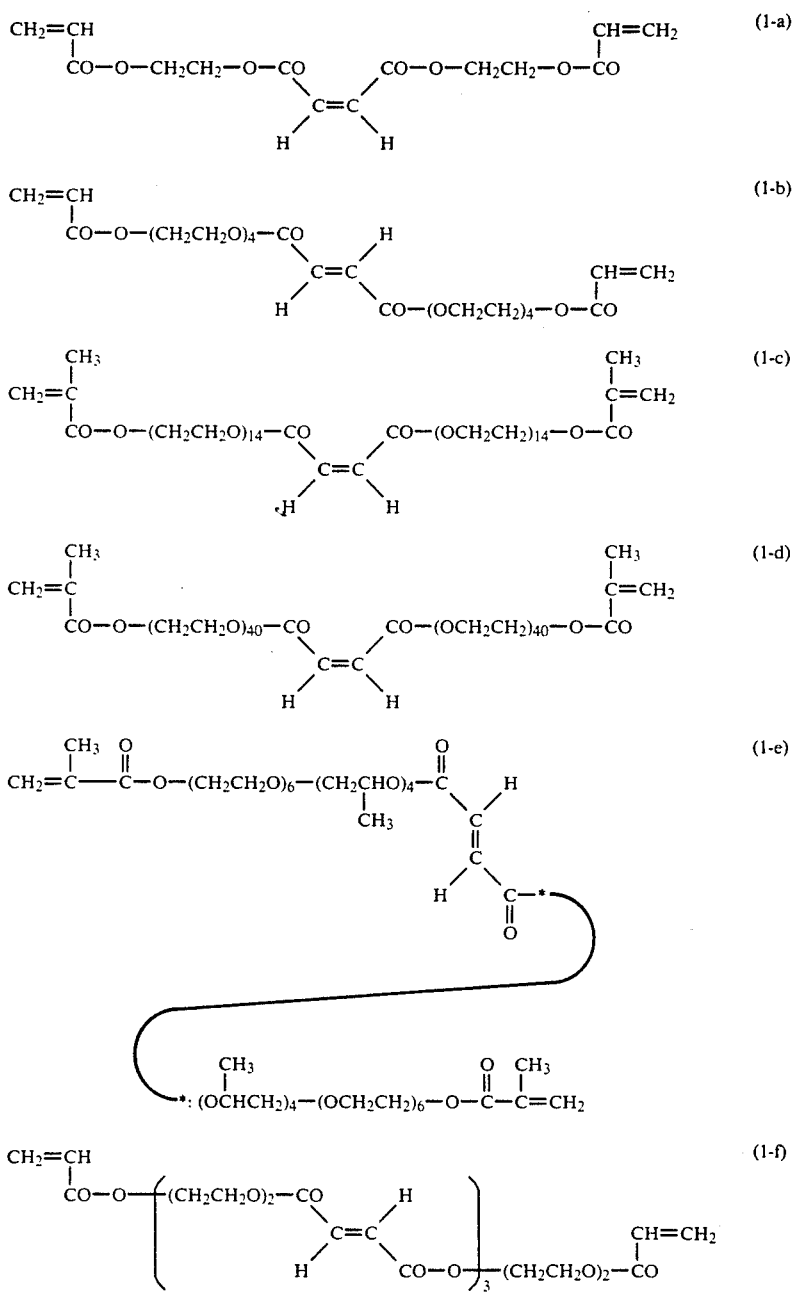

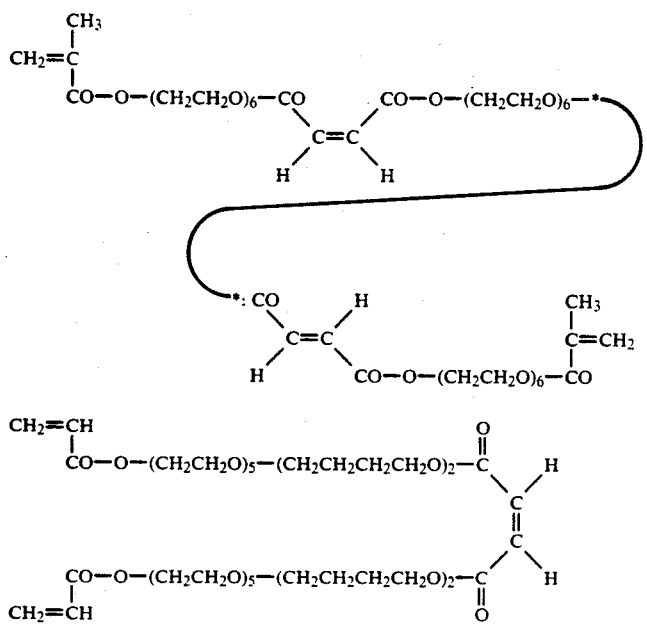

(1-g)

(1-h)
```
CH2=CH                    O
 |                        ||
 CO—O—(CH2CH2O)5—(CH2CH2CH2CH2O)2—C     H
                                   \   /
                                    C
                                    ||
                                    C
                                   /   \
 CO—O—(CH2CH2O)5—(CH2CH2CH2CH2O)2—C     H
 |                        ||
CH2=CH                    O
```

The crosslinking agent (I) used in this invention is obtained by various kinds of methods. For example, it is easily obtained by dehydration condensation of fumaric acid or maleic acid with a polyalkylene glycol in the presence of an acid catalyst, in which the alkylene unit is in a range of from $C_2$ to $C_4$, followed by similar dehydration condensation of (meth)acrylic acid.

In the present invention, a conventional known crosslinking agent (II), if this is a small amount, may be used in combination with the crosslinking agent (I). A preferable amount for use of this crosslinking agent (II) is 20 mole % or less based on the amount for use of the crosslinking agent (I). A preferable crosslinking agent (II) is, for example, such as mentioned in the "BACKGROUND OF THE INVENTION" of this specification text, and one kind or more is used.

An amount for use of the crosslinking agent (I) is not especially limited, but if the absorbent capacity of an obtaining water-absorbent resin is taken into account, it is preferable to use the crosslinking agent (I) in a proportion of from 0.01 to 1 mole % based on the water-soluable monoethylenic unsaturated monomer. If the amount for use of the agent (I) is less than 0.01 mole %, there is a case where the water-soluble ingredient of an obtaining water-absorbent resin becomes large and, if it exceeds 1 mole %, there is a case where the water-absorbent capacity decreases too much.

In this invention, any method can be applied for polymerizing a water-soluble monoethylenic unsaturated monomer in the presence of a crosslinking agent, but the best method is such as polymerizing an aqueous solution of a monomer component containing a water-soluble monoethylenic unsaturated monomer in the presence of a crosslinking agent.

According to this method, only substituting a crosslinking agent in a conventional production method into the crosslinking agent (I) is enough and conventional facilities can be used. Various kinds of methods such as aqueous solution polymerization, reversed-phase suspension polymerization, precipitation polymerization and so forth can be adopted as the present polymerization method. Among these methods, the aqueous solution polymerization method or the reversed-phase suspension polymerization method is preferred from the points of working efficiency during the polymerization reaction and water-absorbent characteristics of an obtaining water-absorbent resin.

Also, there can be used a common method such as a method of polymerizing by using a radical polymerization initiator in initiating the polymerization reaction and a method of polymerizing by irradiating a radiation, an electron beam and ultraviolet rays (in a case of irradiating ultraviolet rays, a photopolymerization initiator is sometimes used.). Preferable radical polymerization initiators are persulfates such as potassium persulfate, sodium persulfate, ammonium persulfate and the like, that are water-soluble radical polymerization initiators of general use; hydroperoxides such as hydrogen peroxide, tertiary-butyl hydroperoxide, cumene hydroperoxide and the like; and azo compounds such as 2,2'-azobis(2-amidinopropane) hydrochloride and the like. These polymerization initiators may be used alone or in combination of two or more kinds. Furthermore, a redox initiator system combined with a reducing agent such as a sulfite, L-ascorbic acid, a ferrous salt and the like may be used. A preferable amount for use of a radical polymerization initiator is a proportion of from 0.001 to 1.0% by weight based on the monomer and a more preferable one is a proportion of from 0.005 to 0.5% by weight.

In synthesizing a water-absorbent resin by an aqueous solution polymerization method or a reversed-phase suspension polymerization method, it is generally preferred to make an aqueous monomer solution. The monomer concentration in this aqueous monomer solution can be chosen in a wide range, but it is generally 20% by weight or more and, preferably, a range of from 25% or more by weight up to a saturated concentration or less. If necessary, in this case an organic solvent may be jointly used. Preferable organic solvents of this type are, for example, alcohols having compatibility with water such as methanol, ethanol, propanol, butanol and the like; ethers having compatibility with water such as tetrahydrofuran, dioxane and the like; ketones having compatibility with water such as acetone, methyl ethyl ketone and the like; nitriles having compatability with water such as acetonitrile and the like; amides having compatibility with water such as N,N-dibutylformamide and the like; and so forth.

It is possible to control the crosslinking density of an obtaining water-absorbent resin by presenting a chain transfer agent in the course of polymerization. Preferable chain transfer agents in this case are, for example, mercaptoethanol, mercaptopropanol, dodecyl mercaptane, thioglycolic acid, thiomalic acid, 3-mercaptopropionic acid, isopropanol, sodium hypophosphite, thiol derivatives of formic acid or formates or the like, thiolic acids, secondary alcohols, hypophosphites and carboxylic acids and so forth.

Although tl polymerization temperature is variable depending upon the sort of the using radical polymerization initiator, it is usually in a range of from 0° to 150° C. or preferably in a range of from 10° to 100° C. The atmospheric pressure during polymerization can be properly set in a range of from a reduced pressure to an added pressure. The polymerization temperature may be controlled by combining at least two factors among the sort and amount of the using radical polymerization initiator and the atmospheric pressure.

A hydrated gel of a water-absorbent resin (a crosslinked polymer containing water) is obtained by the polymerization, finely divided, dried by a common method, crashed if necessary, classified and led to a product. A common drier and heating furnace can be used as a drying method and, for example, a ditch type agitation dryer, rotary dryer, disk dryer, knead dryer, hot wind dryer, fluidized bed dryer, pneumatic convaining dryer, an ultrared radiant dryer, a dielectric heating dryer and so forth are used. Furthermore, the drying may be carried out by azeotropic distillation with an organic solvent.

The water-absorbent resin dried as mentioned above is controlled by, if necessary, crushing and classifying so as to have a desired particle size distribution.

The obtained water-absorbent resin can be improved in absorption characteristics by the following steps: mixing with the crosslinking agent (III) having two or more of a functional group capable of reacting with a functional group which the water-absorbent resin has, letting the crosslinking agent (III) to react on a surface part of the resin, and thereby, heightening the crosslinking density in the neighborhood of the resin surface. Preferable crosslinking agents (III) are, for example in a case where the water-absorbent resin has a carboxyl group, polyvalent alcohols, polyvalent glycidyl ethers, polyvalent amines, polyvalent aziridines, polyvalent isocyanates, polyvalent metal salts and the like.

The water-absorbent resin obtained from the production process of this invention, compared with conventional water-absorbent resins, has high absorption capacity and, because the water-soluble ingredients are small amounts, the sticky feeling of a gel is slight in swelling and the liquid permeability is excellent. Accordingly, the water-absorbent resin can be used in wide fields such as sanitary material, civil engineering, agriculture and gardening and so forth.

In obtaining a water-absorbent resin by copolymerizing a water-soluble monoethylenic unsaturated monomer with a crosslinking agent, a water-absorbent resin having high absorption capacity and water-soluble ingredients in only a small amount is obtained by using the crosslinking agent (I) as a crosslinking agent.

Since the production process of a water-absorbent resin of this invention undergoes a copolymerization reaction of a water-soluble monoethylenic unsaturated monomer in the presence of the crosslinking agent (I) having the above-described specific structure, a water-absorbent resin having high absorption capacity and water-soluble ingredients in only a small amount is obtained according to the process.

DESCRIPTION OF THE PREFERRED EMBODIMENTS

The present invention is illustrated by the following Examples of some preferred embodiments in comparison with Comparative Examples not according to the present invention. However, the present invention is not limited to the following Examples. The absorption capacity and the amount of water-soluble ingredients of the water-absorbent resins obtained from Examples and Comparative Examples were determined as follows.

(a) Absorption capacity

An obtained water-absorbent resin powder, about 0.200 g, was precisely weighed and put uniformly into a tea-bag type bag (40 mm × 50 mm) made of a nonwoven fabric, immersed in a 0.9% saline solution, and the weight of after 30 minutes was determined. Taking the weight of a solution absorbed by only the tea-bag type bag as a blank, the absorption capacity of a water-absorbent resin was calculated according to the following equation (1).

$$\begin{pmatrix} \text{absorption} \\ \text{capacity} \\ (g/g) \end{pmatrix} = \frac{\begin{pmatrix} \text{weight after} \\ \text{absorption (g)} \end{pmatrix} - [\text{blank (g)}]}{\begin{pmatrix} \text{precise weight of} \\ \text{water-absorbent} \\ \text{resin powder (g)} \end{pmatrix}} \quad (1)$$

(b) Amount of water-soluble ingredients

A water-absorbent resin powder, 0.500 g, was dispersed into 1,000 ml of deionized water and, after stirring for 12 hours, this solution was filtered by a filter paper and a solid portion content contained in this filtrate is determined in order to know the content of water-soluble ingredients according to the following equation (2).

$$\begin{pmatrix} \text{amount of} \\ \text{water-soluble} \\ \text{ingredients} \\ (\% \text{ by weight}) \end{pmatrix} = \frac{\begin{pmatrix} \text{weight of} \\ \text{deionized} \\ \text{water (g)} \end{pmatrix} \times \begin{pmatrix} \text{solid portion} \\ \text{content in filtrate} \\ (\% \text{ by weight}) \end{pmatrix}}{0.500 \text{ (g)}} \quad (2)$$

EXAMPLE 1

Into a stainless steel-made twin arm type kneader of 10 liter inner volume equipped with two of a sigma (Σ) type feather and a jacket were added 5,500 g of an aqueous solution of an acrylate-type monomer composed of 75 mole % of sodium acrylate and 25 mole % of acrylic acid (30% by weight in monomer concentration) and 5.37 g (0.05 mole % based on the monomer) of the crosslinking agent (I) shown by the following chemical formula ② (577 in weight average molecular weight), and a nitrogen gas was blown into the obtained mixture to substitute an atmosphere in the reaction system. With warming by running warm water of 35° C. through the jacket, 2.5 g of ammonium persulfate and 2.5 g of sodium hydrogen sulfite were added as a polymerization initiator to the mixture, and a polymerization reaction was initiated with stirring of the sigma (Σ) type feather in the kneader at 65 rpm and then, it was carried out for 1 hour. After completion of the reaction, a finely divided hydrated gel (a crosslinked polymer containing water) was put on a 50 mesh metal net (a Tyler standard sieve) and dried by a hot wind at 150° C. for 2 hours. This dried product was crushed by a hammer mill to obtain a water-absorbent resin.

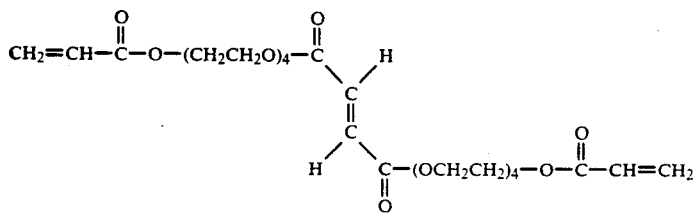

EXAMPLE 2

The procedure of Example 1 was repeated except that 13.58 g (0.05 mole % based on the monomer) of a compound shown by the following chemical formula ③ (1458 in weight average molecular weight) was used as the crosslinking agent (I), whereby a water-absorbent resin was obtained.

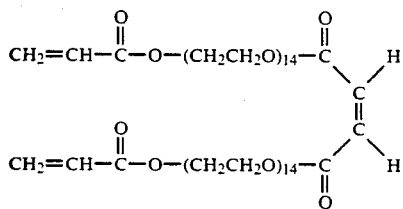

EXAMPLE 3

The procedure of Example 1 was repeated except that 7.20 g (0.05 mole % based on the monomer) of a compound shown by the following chemical formula ④ (773 in weight average molecular weight) was used as the crosslinking agent (I), whereby a water-absorbent resin was obtained.

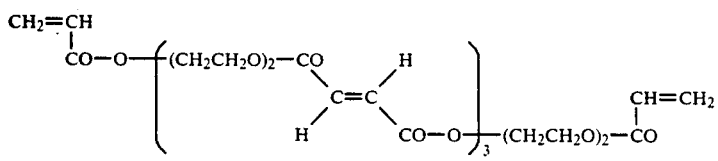

COMPARATIVE EXAMPLE 1

The procedure of Example 1 was repeated except that 1.65 g (0.03 mole % based on the monomer) of trimethylolpropane triacrylate was used instead of the crosslinking agent (I), whereby a water-absorbent resin was obtained.

COMPARATIVE EXAMPLE 2

The procedure of Example 1 was repeated except that 4.87 g (0.05 mole % based on the monomer) of polyethylene glycol diacrylate (9 in the average unit number of ethylene oxide) was used instead of the crosslinking agent (I), whereby a water-absorbent resin was obtained.

The absorption capacity and amounts of water-soluble ingredients of water-absorbent resins obtained from the above-described Examples and Comparative Examples were determined and summarized in Table 1.

TABLE 1

| | Evaluation of water-absorbent resin | |
|---|---|---|
| | Absorption capacity (g/g) | Water-soluble ingredient (% by weight) |
| Example 1 | 59.7 | 11.4 |
| Example 2 | 55.3 | 12.0 |
| Example 3 | 57.4 | 10.5 |
| Com. Ex. 1 | 58.3 | 19.7 |
| Com. Ex. 2 | 43.2 | 12.1 |

EXAMPLE 4

Into a 500 ml four-neck separable flask equipped with a stirrer, reflux condenser, thermometer, nitrogen gas-introducing tube and dropping funnel were charged and dissolved 250 ml of cyclohexane and 20 g of sorbitan monostearate, that is a disperser, and a nitrogen gas was blown into the obtained mixture to substitute an atmosphere in the reaction system. Into another flask were prepared a solution of 28.2 g of sodium acrylate, 7.21 g of acrylic acid, and 0.498 g (0.1 mole % based on the monomer) of the crosslinking agent (I) shown by the following chemical formula ⑤ (1246 in weight average molecular weight) in 65.8 g of ion-exchanged water and, to this solution, 0.05 g of potassium persulfate was added and dissolved, and a nitrogen gas was blown into the obtained mixture solution to substitute the flask inside atmosphere. At this time, the monomer concentration in this aqueous solution was 35% by weight. The aqueous solution of polymerizable monomers in this flask was added into the aforementioned separable flask. The obtained mixture was stirred at 250 rpm to disperse it in cyclohexane, warmed up to a solution temperature of 60° C. to initiate a polymerization reaction and, further, ripened at this temperature for 2 hours to obtain a polymer-dispersed solution.

Then, a most part of water contained in the polymer was removed by azeotropic dehydration and further, cyclohexane was removed. An obtained residue was dried at 80° C. under a reduced pressure to ontain a water-absorbent resin.

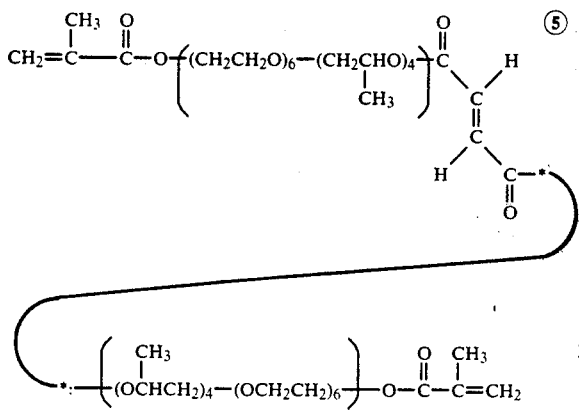

(5)

EXAMPLE 5

The procedure of Example 4 was repeated except that 0.306 g (0.1 mole % based on the monomer) of a compound (753 in weight average molecular weight) shown by the following chemical formula (6) was used as the crosslinking agent (I), whereby a water-absorbent resin was obtained.

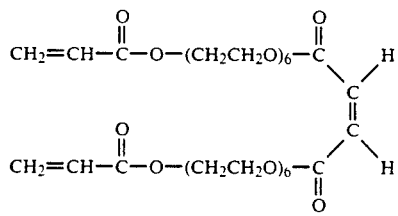

(6)

COMPARATIVE EXAMPLE 3

The procedure of Example 4 was repeated except that 0.0309 g (0.05 mole % based on the monomer) of N,N'-methylenebis(acrylamide) was used instead of the crosslinking agent (I), whereby a water-absorbent resin was obtained.

COMPARATIVE EXAMPLE 4

The procedure of Example 4 was repeated except that 0.308 g (0.1 mole % based on the monomer) of polyethylene glycol diacrylate (14 in average unit number of ethylene oxide) was used instead of the crosslinking agent (I), whereby a water-absorbent resin was obtained.

The absorption capacity and amounts of water-soluble ingredients of water-absorbent resins obtained from the above-described Examples and Comparative Examples were determined and summarized in Table 2.

TABLE 2

| | Evaluation of water-absorbent resin | |
|---|---|---|
| | Absorption capacity (g/g) | Water-soluble ingredient (% by weight) |
| Example 4 | 49.5 | 9.0 |
| Example 5 | 44.4 | 7.1 |
| Comp. Ex. 3 | 43.9 | 16.5 |
| Comp. Ex. 4 | 34.2 | 8.4 |

As seen in Tables 1 and 2, the water-absorbent resins obtained from Examples are high in the absorption capacity and small in the amounts of water-soluble ingredients. In contrast, if the water-absorbent resins obtained from Comparative Examples become high in the absorption capacity, the amounts of water-soluble ingredients become large, and if the amounts of water-soluble ingredients become small, the absorption capacity becomes low.

What is claimed is:

1. A process for producing a water-absorbent resin, comprising polymerizing a water-soluble monoethylenic unsaturated monomer in the presence of a crosslinking agent, wherein said crosslinking agent is a compound represented by the following formula

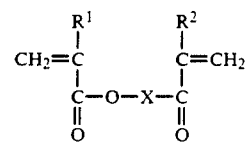

1 wherein $R^1$ and $R^2$ denote a hydrogen atom or a methyl group independently;

X denotes a divalent, straight chain organic group comprising structural units A, B and optionally C, wherein A is 1 to 5 units of $-CO-CH=CH-CO-O-$, B is 2 to 100 units of $-CH_2CH_2O-$, and C is 0 to 20 units of $-R^3O-$, wherein $R^3$ is a branched or straight chain $C_3-C_4$ alkylene, with the provisos (i) that B should be located on both sides of structural unit A when X includes structural units A and B, but not C, and (ii) that at least one of B and C may be located on both sides of structural unit A when X includes A, B and C.

2. A process for producing a water-absorbent resin as claimed in claim 1, wherein the crosslinking agent is used in a proportion of from 0.01 to 1 mole % based on the water-soluble monoethylenic unsaturated monomer.

3. A process for producing a water-absorbent resin as claimed in claim 1 or 2, wherein a polymerization reaction is carried out by using an aqueous monomer solution containing a water-soluble monoethylenic unsaturated monomer as a main component.

4. A process for producing a water-absorbent resin as claimed in claim 3, wherein the concentration of the water-soluble monoethylenic unsaturated monomer in the aqueous monomer solution is in a range of from 20% by weight up to a concentration of saturation.

* * * * *